United States Patent
Yoshimura et al.

(10) Patent No.: US 10,457,636 B2
(45) Date of Patent: Oct. 29, 2019

(54) PRODUCTION METHOD OF ε-CAPROLACTAM

(71) Applicant: Sumitomo Chemical Company, Limited, Tokyo (JP)

(72) Inventors: Kazuaki Yoshimura, Niihama (JP); Nobufumi Watanabe, Tsukuba (JP); Kohei Seki, Ichihara (JP); Masashi Teramori, Niihama (JP); Keisuke Tanaka, Niihama (JP)

(73) Assignee: Sumitomo Chemical Company, Limited, Tokyo (JP)

(*) Notice: Subject to any disclaimer, the term of this patent is extended or adjusted under 35 U.S.C. 154(b) by 0 days.

(21) Appl. No.: 16/318,791

(22) PCT Filed: Sep. 7, 2017

(86) PCT No.: PCT/JP2017/032205
§ 371 (c)(1),
(2) Date: Jan. 18, 2019

(87) PCT Pub. No.: WO2018/051869
PCT Pub. Date: Mar. 22, 2018

(65) Prior Publication Data
US 2019/0241513 A1   Aug. 8, 2019

(30) Foreign Application Priority Data

Sep. 14, 2016 (JP) ................. 2016-179279

(51) Int. Cl.
C07D 201/04 (2006.01)
C01B 39/36 (2006.01)
B01J 29/40 (2006.01)

(52) U.S. Cl.
CPC ............ C07D 201/04 (2013.01); B01J 29/40 (2013.01); C01B 39/36 (2013.01)

(58) Field of Classification Search
CPC .................................................. C07D 201/04
See application file for complete search history.

(56) References Cited

U.S. PATENT DOCUMENTS

| | | |
|---|---|---|
| 5,312,915 A | 5/1994 | Yashima et al. |
| 5,741,904 A | 4/1998 | Hoelderich et al. |
| 2006/0004194 A1 | 1/2006 | Hoshino et al. |
| 2007/0135637 A1 | 6/2007 | Bosch et al. |
| 2016/0167030 A1* | 6/2016 | Levy ............... B01J 29/84 540/464 |

FOREIGN PATENT DOCUMENTS

| | | |
|---|---|---|
| EP | 2599748 A1 | 6/2013 |
| EP | 2617680 A1 | 7/2013 |
| JP | H5170732 A | 7/1993 |
| JP | H6-256304 A | 9/1994 |
| JP | H912540 A | 1/1997 |
| JP | 2001-181260 A | 7/2001 |
| JP | 2001-213862 A | 8/2001 |
| JP | 2006-16220 A | 1/2006 |
| JP | 2007-533580 A | 11/2007 |
| JP | 2009-190930 A | 8/2009 |
| JP | 2012-158201 A | 8/2012 |
| JP | 2013-112577 A | 6/2013 |
| JP | 2013-147356 A | 8/2013 |

OTHER PUBLICATIONS

Int'l Search Report dated Nov. 21, 2017 in Int'l Application No. PCT/JP2017/032205.
Muroi et al, "Shokubai kara Miru Kagaku Kogyo no Mirai-23 Caprolacam Shinpo", Gekkan Fine Chemical, vol. 40, Issue 1, pp. 65-68, Dec. 15, 2010.

* cited by examiner

Primary Examiner — Bruck Kifle
(74) Attorney, Agent, or Firm — Panitch Schwarze Belisario & Nadel LLP

(57) ABSTRACT

A method for producing ε-caprolactam involves a step of Beckmann-rearranging cyclohexanone oxime in a gas phase in the presence of a zeolite catalyst containing silicon and at least one element selected from alkaline earth metal elements and magnesium. The concentration of the above-described element in the zeolite catalyst is 3 ppm by mass or more and 10000 ppm by mass or less.

5 Claims, 2 Drawing Sheets

[Fig. 1]
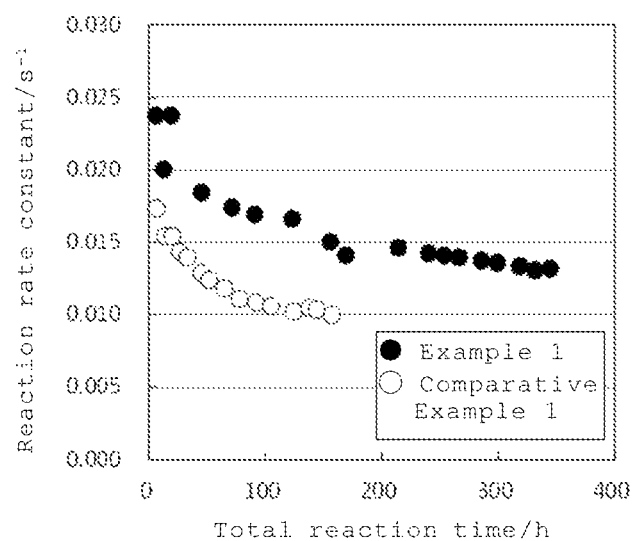
[Fig. 2]
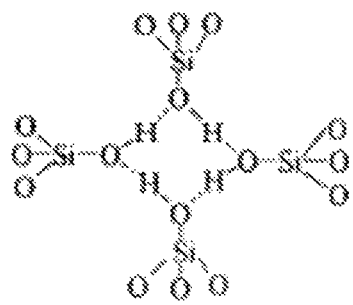

[Fig. 3]
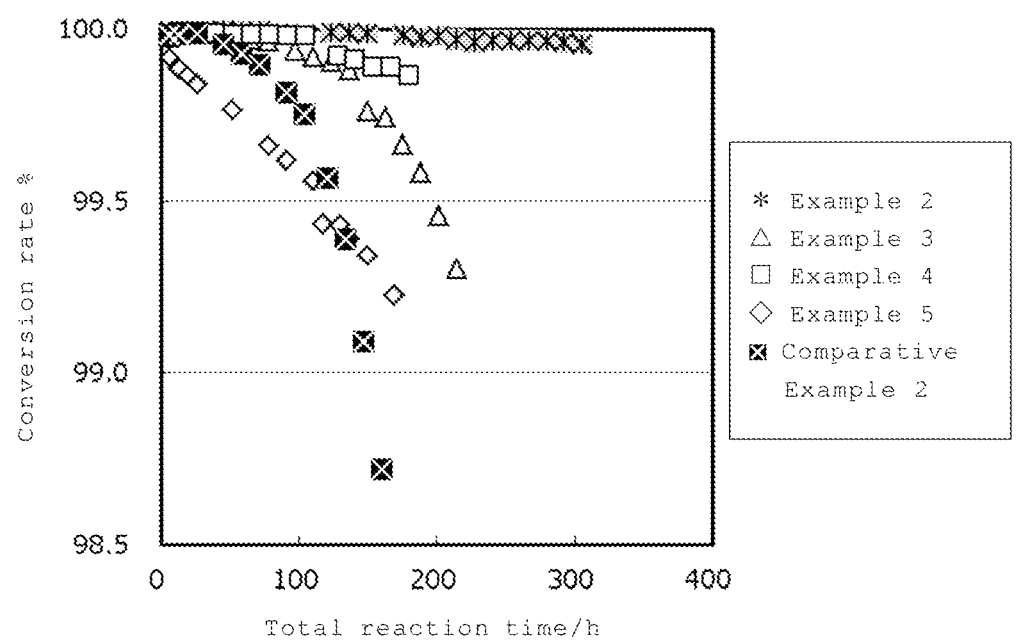

PRODUCTION METHOD OF ε-CAPROLACTAM

CROSS-REFERENCE TO RELATED APPLICATION

This application is a Section 371 of International Application No. PCT/JP2017/032205, filed Sep. 7, 2017, which was published in the Japanese language on Mar. 22, 2018 under International Publication No. WO 2018/051869 A1, which claims priority under 35 U.S.C. § 119(b) to Japanese Application No. 2016-179279, filed Sep. 14, 2016, the disclosures of which are incorporated herein by reference in their entirety.

TECHNICAL FIELD

The present invention relates to a production method of ε-caprolactam, comprising a step of Beckmann-rearranging cyclohexanone oxime in a gas phase in the presence of a zeolite catalyst.

BACKGROUND ART

As one method for producing ε-caprolactam, a method of Beckmann-rearranging cyclohexanone oxime in a gas phase using zeolite as a catalyst is conventionally known. For example, Patent Document 1 suggests a method using a solid catalyst obtained by contacting with ammonia water or with an aqueous solution composed of an ammonium salt and at least one basic substance selected from ammonia, lower alkylamine, allylamine and alkylammonium hydroxide as a catalyst. Further, Patent Document 2 suggests a method for producing ε-caprolactam by Beckmann rearrangement of cyclohexanone oxime in a gas phase at a temperature in the range of 250 to 450° C. in contact with a zeolite catalyst.

PRIOR ART DOCUMENT

Patent Document

[Patent Document 1] Japanese Unexamined Patent Application Publication (JP-A) No. hei-5-170732
[Patent Document 2] JP-A No. hei-9-12540

SUMMARY OF THE INVENTION

Problem to be Solved by the Invention

In the production methods described in the above-described patent documents, however, it is difficult to continuously produce ε-caprolactam by reacting cyclohexanone oxime at a high conversion rate over a long period of time, thus, productivity thereof is not satisfactory, since the initial catalytic activity is low and the catalytic activity lowers with the passage of time.

The present invention has an object of providing an ε-caprolactam production method giving high initial catalytic activity, capable of maintaining high catalytic activity over a long period of time and excellent in productivity.

Means for Solving the Problem

The present inventors have intensively studied and resultantly found that the above-described object can be attained by using a zeolite catalyst containing a silicon element and at least one element selected from the group consisting of alkaline earth metal elements and a magnesium element, leading to the completion of the present invention.

That is, the present invention provides a production method of ε-caprolactam, comprising a step of Beckmann-rearranging cyclohexanone oxime in a gas phase in the presence of a zeolite catalyst containing a silicon element and at least one element selected from the group consisting of alkaline earth metal elements and a magnesium element, wherein the concentration of the above-described at least one element selected from the group consisting of alkaline earth metal elements and a magnesium element in the above-described zeolite catalyst is 3 ppm by mass or more and 10000 ppm by mass or less.

Effect of the Invention

The present invention can provide an ε-caprolactam production method giving high initial catalytic activity, capable of maintaining high catalytic activity over a long period of time and excellent in productivity.

BRIEF EXPLANATION OF DRAWINGS

FIG. 1 is a view showing a change of the reaction rate constant in Example 1 and Comparative Example 1.
FIG. 2 is a view showing the structure of the nest silanol.
FIG. 3 is a view showing a change of the conversion rate of cyclohexanone oxime in Examples 2 to 5 and Comparative Example 2.

MODES FOR CARRYING OUT THE INVENTION

The zeolite catalyst used in the present invention is a catalyst containing a silicon element and at least one element (hereinafter, referred to as element A in some cases) selected from the group consisting of alkaline earth metal elements and a magnesium element, and specifically a catalyst containing a silicon element, an oxygen element and the element A. The above-described zeolite catalyst may contain other elements than those described above.

The element A includes alkaline earth metal elements such as a calcium element, a strontium element, a barium element and the like, and a magnesium element and the like, and is preferably a magnesium element.

The concentration of the element A in the above-described zeolite catalyst is 3 ppm by mass or more and 10000 ppm by mass or less, preferably 5 ppm by mass or more and 5000 ppm by mass or less, more preferably 5 ppm by mass or more and 2000 ppm by mass or less, further preferably 5 ppm by mass or more and 300 ppm by mass or less, still more preferably 20 ppm by mass or more and 300 ppm by mass or less. By using the zeolite catalyst having the concentration of the element A in the above-described range, high catalytic activity can be maintained over a long period of time and ε-caprolactam can be produced with good productivity, and additionally, the initial selectivity of ε-caprolactam can be more enhanced. The concentration of the element A in the zeolite catalyst can be measured by inductively coupled plasma-atomic emission spectrometry (ICP-AES method) or inductively coupled plasma-mass spectrometry (ICP-MS method). When the concentration of the element A in the zeolite catalyst is smaller (for example, 10 ppm by mass or less), it is preferably measured by inductively coupled plasma-mass spectrometry (ICP-MS method), and if not, it is preferably measured by inductively coupled plasma-atomic emission spectrometry (ICP-AES method).

The production method of the above-described zeolite catalyst includes a method containing a step (mixing step) of mixing zeolite with a solution containing a compound having the element A, and the like.

The above-described zeolite is one containing a silicon element and an oxygen element as the skeleton constituent element, and may be a crystalline silica of which skeleton is constituted of a silicon element and an oxygen element, and may also be a crystalline metallosilicate containing further other elements (excluding the element A) as the skeleton constituent element.

The above-described zeolite, those having various structures are known, and of them, those having a pentasil type structure are preferable. The pentasil type structure includes ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WEI, WEN, YUG and ZON structures, or structures combining two or more of them. As the zeolite having the pentasil type structure, those having the MFI structure are preferable. The structure of the above-described zeolite can be analyzed using an X-ray diffraction apparatus.

As the above-described zeolite, those having a nest silanol are preferable. The nest silanol is a structure having a zeolite skeleton mainly constituted of a silicon element and an oxygen element in which the T-site is deficient, as a result, four silanols become adjacent and hydroxyl groups are mutually hydrogen-bonded, and specifically, it is a structure as shown in FIG. 2. The above-described nest silanol is recognized as a peak near 3500 cm$^{-1}$ in infrared spectroscopy spectrum. By mixing zeolite having the above-described nest silanol and a solution containing a compound having the element A, the element A is easily inserted into the zeolite skeleton, and a catalyst having higher activity can be obtained, and productivity can be improved.

Zeolite having the nest silanol can be produced by methods described in Patent Document 1, Patent Document 2, JP-A No. 2013-147356, JP-A No. 2017-30986 and the like, and for example, can be produced by a method containing the following step (1) and the following step (2) in this order.

Step (1): a step of reacting a mixture containing a silicon compound and at least one compound selected from the group consisting of boron compounds and germanium compounds, to obtain a zeolite crystal.

Step (2): a step of contact-treating the above-described zeolite crystal with an aqueous solution containing at least one acid selected from the group consisting of inorganic acids and organic acids.

The at least one compound selected from the group consisting of boron compounds and germanium compounds includes boric acid, ammonium borate, ammonium tetrafluoroborate, lithium metaborate, lithium tetraborate, lithium tetrafluoroborate, sodium metaborate, sodium tetraborate, sodium perborate, sodium tetrahydroborate, sodium tetraethylborate, sodium tetraphenylborate, sodium tetrafluoroborate, potassium metaborate, potassium tetraborate, potassium pentaborate, potassium tetrafluoroborate, calcium borate, magnesium borate, zinc borate, trimethyl borate, trimethylene borate, triethyl borate, tetrafluoroboric acid, tri-n-butylboric acid, triisopropyl borate, triethanolamine borate, nitrosyl tetrafluoroborate, germanium oxide, germanium chloride, germanium bromide, germanium iodide, tetraethylgermanium, tetramethylgermanium, tetraisopropoxygermanium and the like, and is preferably boric acid, trimethyl borate, triethyl borate or germanium oxide. These may be used singly or in combination of two or more kinds thereof.

The silicon compound includes tetraalkyl orthosilicates, colloidal silica, fumed silica, alkali metal silicates, magnesium, and alkaline earth metal silicates and the like, preferably, tetraalkyl orthosilicates.

The mixture containing a silicon compound and at least one compound selected from the group consisting of boron compounds and germanium compounds may contain water and a structure directing agent, and basic compounds such as sodium hydroxide, potassium hydroxide and the like.

The structure directing agent denotes an organic compound which is utilized to form the zeolite structure. The above-described structure directing agent can form a precursor of the zeolite structure by placing a polysilicate ion or a polymetallosilicate ion around it (see, Science and Engineering of Zeolite, Kodansha Scientific, 2000, pp. 33-34). The structure directing agent includes, for example, quaternary ammonium hydroxide, sodium hydroxide, pentaerythritol, dipropylamine, cyclohexylamine, hexamethyleneimine and the like, and is preferably quaternary ammonium hydroxide.

The quaternary ammonium hydroxide includes, for example, compounds represented by the following formula (I), preferably, tetraalkylammonium hydroxides.

$$R^1R^2R^3R^4N^+OH^- \quad (I)$$

(in the formula (I), $R^1$, $R^2$, $R^3$ and $R^4$ each independently represent an alkyl group, an alkenyl group, an aralkyl group or an aryl group. $R^1$, $R^2$, $R^3$ and $R^4$ may be mutually the same group or different groups.)

The tetraalkylammonium hydroxide includes, for example, tetramethylammonium hydroxide, tetraethyl hydroxide, tetra-n-propylammonium hydroxide, tetra-n-butylammonium hydroxide, triethylmethylammonium hydroxide, tri-n-propylmethylammonium hydroxide, tri-n-butylmethylammonium hydroxide and the like, and is preferably tetra-n-propylammonium hydroxide.

The amount of a silicon element contained in a mixture containing a silicon compound and at least one compound selected from the group consisting of boron compounds and germanium compounds is preferably 5 mol or more and 100 mol or less with respect to 1 mol of the total amount of a boron element and a germanium element contained in the mixture.

The method of reacting a mixture containing a silicon compound and at least one compound selected from the group consisting of boron compounds and germanium compounds includes, for example, a method of subjecting the mixture to a hydrothermal synthesis reaction, and the like. The hydrothermal synthesis reaction is a reaction of synthesizing a compound or growing a crystal under heating and pressure. The reaction temperature in being subjected to the hydrothermal synthesis reaction is, for example, 80° C. or more and 160° C. or less, the reaction time is, for example, 1 hour or more and 200 hours or less, and the pressure in the reaction is, for example, 0.1 MPa or more and 5 MPa or less. The method of the hydrothermal synthesis reaction is not particularly restricted, and for example, the above-described mixture is sealed in a reaction vessel such as an autoclave and the like, and in a sealed state, stirred under the above-described reaction temperature and pressure conditions.

After reacting a mixture containing a silicon compound and at least one compound selected from the group consisting of boron compounds and germanium compounds, if necessary, solid-liquid separation such as concentration, filtration, decantation and the like, washing treatments with water or an organic solvent such as methanol, ethanol and the like, and operations such as drying, calcination and the like can be conducted, to obtain a zeolite crystal.

Calcination is suitably conducted, usually, under an atmosphere of an oxygen-containing gas, for example, under an air atmosphere or under an atmosphere of a mixed gas of air and nitrogen at a temperature of 400° C. or more and 600° C. or less. The calcination time is, for example, 0.5 hours or more and 12 hours or less.

The amount of a silicon element contained in the zeolite crystal obtained in the above-described step (1) is preferably 5 mol or more and 400 mol or less, more preferably 10 mol or more and 400 mol or less with respect to 1 mol of the total amount of a boron element and a germanium element contained in the zeolite crystal. The amount of boron and germanium elements contained in the zeolite crystal can be determined, for example, by inductively coupled plasma (ICP)-atomic emission spectrometry. The amount of a silicon element can be determined, for example, by ICP-atomic emission spectrometry, or can be determined by subtracting the content of elements other than a silicon element from the total amount of elements contained in the calcined zeolite crystal.

The inorganic acid used in the above-described step (2) includes nitric acid, hydrochloric acid, sulfuric acid, phosphoric acid and the like, and the organic acid includes formic acid, acetic acid, propionic acid, benzoic acid, citric acid, oxalic acid, terephthalic acid, p-toluenesulfonic acid and the like. These may be used singly or in combination of two or more kinds thereof. The at least one acid selected from the group consisting of inorganic acids and organic acids is preferably an inorganic acid, more preferably nitric acid or hydrochloric acid, further preferably nitric acid.

The hydrogen ion concentration of at least one acid selected from the group consisting of inorganic acids and organic acids contained in an aqueous solution containing the at least one acid selected from the group consisting of inorganic acids and organic acids is preferably 0.001 mol/L or more and 20 mol/L or less. Further, the above-described aqueous solution may contain salts such as ammonium nitrate, ammonium chloride, ammonium sulfate, ammonium carbonate and the like in addition to the above-described at least one acid selected from the group consisting of inorganic acids and organic acids. The use amount of the aqueous solution is preferably 80 parts by weight or more and 5000 parts by weight or less with respect to 100 parts by weight of the zeolite catalyst.

"Contact-treating the zeolite crystal with an aqueous solution" in the above-described step (2) means that the zeolite crystal is brought into contact with the aqueous solution. By the above-described step (2), a boron element, a germanium element and the like incorporated into the zeolite crystal can be removed. The temperature in the contact treatment is, for example, 0° C. or more and 100° C. or less, the pressure applied in the contact treatment is, for example, 0.1 MPa or more and 5 MPa or less, and the treatment time in the contact treatment is, for example, 0.1 hour or more and 100 hours or less. The contact treatment may be conducted in batch-wise mode or may be conducted in continuous mode, and for example, the zeolite crystal calcined in a stirring tank may be immersed in the above-described aqueous solution and stirred, or the above-described aqueous solution may be passed through a tubular vessel filled with the calcined zeolite crystal. When conducted in batch-wise mode, it is possible to perform the above-described contact treatment again after solid-liquid separation described later. The number of the contact treatment is, for example, once or more and 10 times or less.

After the contact treatment, if necessary, solid-liquid separation such as concentration, filtration, decantation and the like, washing treatments with water or an organic solvent such as methanol, ethanol and the like, and operations such as drying and the like can be conducted, to obtain zeolite having the nest silanol.

The compound having the above-described element A used in producing the zeolite catalyst includes halides, oxo acid salts (nitric acid salts, carbonic acid salts, sulfuric acid salts, silicic acid salts and the like), organic acid salts (acetic acid salts, citric acid salts and the like), oxides, hydroxides, sulfides, hydrides and the like having the above-described element A, and of them, halides, nitric acid salts, carbonic acid salts, oxides or hydroxides are preferable, and halides or nitric acid salts are more preferable. The halide having the above-described element A is preferably a chloride. The compounds having the above-described element A may be used in combination of two or more kinds thereof.

The compound having a magnesium element includes magnesium halides such as magnesium fluoride ($MgF_2$), magnesium chloride ($MgCl_2$), magnesium bromide ($MgBr_2$), magnesium iodide ($MgI_2$) and the like; oxo acid magnesium salts such as magnesium carbonate ($MgCO_3$), magnesium sulfate ($MgSO_4$), magnesium sulfite ($MgSO_3$), magnesium nitrate ($Mg(NO_3)_2$), magnesium nitrite ($Mg(NO_2)_2$), magnesium thiosulfate ($MgS_2O_3$), magnesium silicate ($MgO.nSiO_2$, n=1 to 4 [molar ratio]), magnesium phosphate ($MgHPO_4$), magnesium borate ($MgB_2O_4$) and the like; oxides and hydroxides such as magnesium oxide (MgO), magnesium peroxide ($MgO_2$), magnesium hydroxide ($Mg(OH)_2$) and the like; organic acid magnesium salts such as magnesium acetate ($Mg(CH_3COO)_2$), magnesium citrate and the like; magnesium hydride ($MgH_2$); magnesium sulfide (MgS) and the like, and when hydrates thereof are present, the hydrate may be used. Further, these compounds may be used in combination of two or more kinds thereof.

The compound having a calcium element includes calcium halides such as calcium fluoride ($CaF_2$), calcium chloride ($CaCl_2$), calcium bromide ($CaBr_2$), calcium iodide ($CaI_2$) and the like; oxo acid calcium salts such as calcium carbonate ($CaCO_3$), calcium sulfate ($CaSO_4$), calcium sulfite ($CaSO_3$), calcium nitrate ($Ca(NO_3)_2$), calcium nitrite ($Ca(NO_2)_2$), calcium thiosulfate ($CaS_2O_3$), calcium silicate ($CaO.nSiO_2$, n=1 to 4 [molar ratio]), calcium phosphate ($CaHPO_4$), calcium borate ($CaB_2O_4$) and the like; oxides and hydroxides such as calcium oxide (CaO), calcium peroxide ($CaO_2$), calcium hydroxide ($Ca(OH)_2$) and the like; organic acid calcium salts such as calcium acetate ($Ca(CH_3COO)_2$), calcium citrate and the like; calcium hydride ($CaH_2$); calcium sulfide (CaS) and the like, and when hydrates thereof are present, the hydrate may be used. Further, these compounds may be used in combination of two or more kinds thereof.

The compound having a strontium element includes strontium halides such as strontium fluoride ($SrF_2$), strontium chloride ($SrCl_2$), strontium bromide ($SrBr_2$), strontium iodide ($SrI_2$) and the like; oxo acid strontium salts such as strontium carbonate ($SrCO_3$), strontium sulfate ($SrSO_4$), strontium sulfite ($SrSO_3$), strontium nitrate ($Sr(NO_3)_2$), strontium nitrite ($Sr(NO_2)_2$), strontium thiosulfate ($SrS_2O_3$), strontium silicate ($SrO \cdot nSiO_2$, n=1 to 4 [molar ratio]), strontium phosphate ($SrHPO_4$), strontium borate ($SrB_2O_4$) and the like; oxides and hydroxides such as strontium oxide (SrO), strontium peroxide ($SrO_2$), strontium hydroxide ($Sr(OH)_2$) and the like; organic acid strontium salts such as strontium acetate ($Sr(CH_3COO)_2$), strontium citrate and the like; strontium hydride ($SrH_2$); strontium sulfide (SrS) and the like, and when hydrates thereof are present, the hydrate may be used. Further, these compounds may be used in combination of two or more kinds thereof.

The compound having a barium element includes barium halides such as barium fluoride ($BaF_2$), barium chloride ($BaCl_2$), barium bromide ($BaBr_2$), strontium iodide ($BaI_2$) and the like; oxo acid barium salts such as barium carbonate ($BaCO_3$), barium sulfate ($BaSO_4$), barium sulfite ($BaSO_3$), barium nitrate ($Ba(NO_3)_2$), barium nitrite ($Ba(NO_2)_2$), barium thiosulfate ($BaS_2O_3$), barium silicate ($BaO \cdot nSiO_2$, n=1 to 4 [molar ratio]), barium phosphate ($BaHPO_4$), barium borate ($BaB_2O_4$) and the like; oxides and hydroxides such as barium oxide (BaO), barium peroxide ($BaO_2$), barium hydroxide ($Ba(OH)_2$) and the like; organic acid barium salts such as barium acetate ($Ba(CH_3COO)_2$), barium citrate and the like; barium hydride ($BaH_2$); barium sulfide (BaS) and the like, and hydrates thereof may be used. If necessary, these may be used in combination of two or more kinds thereof.

The solvent used in a solution containing a compound having the element A includes organic solvents such as methanol, ethanol and the like, and water and the like, and water is preferable. The concentration of the solution containing a compound having the element A is preferably 0.001 m mol/L or more and 1000 m mol/L or less, more preferably 0.01 m mol/L or more and 10 m mol/L or less.

In the above-described mixing step, an ammonia aqueous solution may be mixed, and for the purpose of removing a compound having the excess element A contained in the product, ammonium salts such as ammonium nitrate, ammonium chloride, ammonium sulfate, ammonium carbonate, tetrapropylammonium bromide and the like may be mixed. The temperature in the above-described mixing step is preferably 0° C. or more and 100° C. or less, more preferably 60° C. or more and 100° C. or less, further preferably 70° C. or more and 100° C. or less. The pressure in the above-described mixing step is preferably 0.1 MPa or more and 5 MPa or less. The mixing time in the above-described mixing step is preferably 0.1 hour or more and 100 hours or less. The above-described mixing step may be conducted several times.

After the above-described mixing step, a step of washing the resultant zeolite catalyst (washing step I) may be conducted. By performing the washing step I, excess element A and a compound having the element A contained in the zeolite catalyst can be removed. The solvent used in the washing step I includes organic solvents such as methanol, ethanol and the like, and water and the like. The temperature in the above-described washing step I is preferably 0° C. or more and 100° C. or less, more preferably 60° C. or more and 100° C. or less, further preferably 70° C. or more and 100° C. or less. It is preferable that the temperature in the above-described washing step I is higher since excess element A and a compound having the element A contained in the product can be removed more efficiently. The pressure in the above-described washing step I is preferably 0.1 MPa or more and 5 MPa or less. The time of washing step I is preferably 0.1 hour or more and 100 hours or less. The washing treatment may be conducted in batch-wise mode or may be conducted in continuous mode, and for example, the zeolite catalyst may be immersed in water or the like and stirred in a stirring tank, or water or the like may be passed through a tubular vessel filled with the zeolite catalyst. In the case of batch-wise mode, the washing step I can be conducted several times, and the number of the washing step I is preferably once or more and 40 times or less.

After the above-described mixing step, or after the above-described mixing step and the washing step I, a step of mixing the resultant zeolite catalyst with a solution containing an acid (acid treatment step) may be conducted. By performing the above-described acid treatment step, excess element A and a compound containing the element A contained in the zeolite catalyst can be removed, and cyclohexanone oxime can be reacted at higher conversion rate, and ε-caprolactam can be produced at higher selectivity.

The solution containing an acid is preferably an aqueous solution containing an inorganic acid, an aqueous solution containing an organic acid or an aqueous solution containing an inorganic acid and an organic acid. The inorganic acid includes nitric acid, hydrochloric acid, chloric acid, chlorous acid, hypochlorous acid, perchloric acid, hydrobromic acid, sulfuric acid, sulfurous acid, phosphoric acid, phosphorus acid and the like. The organic acid includes formic acid, acetic acid, propionic acid, butyric acid, 2,2-dimethylpropanoic acid, benzoic acid, citric acid, oxalic acid, malonic acid, succinic acid, glutaric acid, adipic acid, acrylic acid, methacrylic acid, maleic acid, fumaric acid, meta-phthalic acid, ortho-phthalic acid, terephthalic acid, cyclohexanecarboxylic acid, mesitylenecarboxylic acid, phenol, ortho-cresol, meta-cresol, para-cresol, 2,4-dimethylphenol, 2,4,6-trimethylphenol, cyclohexanesulfonic acid, ortho-toluenesulfonic acid, meta-toluenesulfonic acid, para-toluenesulfonic acid, 2,4-dimethylbenzenesulfonic acid, 3,5-dimethylbenzenesulfonic acid, mesirylenesulfonic acid and the like. Each of the inorganic acid and the organic acid may be used in combination of two or more kinds thereof.

In the above-described solution containing an acid, the concentration of an acid ($H^+$ concentration) may be controlled depending on the amount of the element A used in the above-described mixing step, and is, for example, 0.001 m mol/L or more and 20 m mol/L or less. The addition amount of the above-described solution containing an acid may be controlled depending on the amount of the element A used in the above-described mixing step, and for example, is an amount containing an acid in an amount of 0.1 time or more and 100 times or less of the amount of the element A used in the above-described mixing step.

The temperature in the acid treatment step is preferably 0° C. or more and 100° C. or less, and the pressure in the acid treatment step is preferably 0.1 MPa or more and 5 MPa or less. The treatment time in the acid treatment is preferably 0.1 hour or more and 100 hours or less. The acid treatment may be conducted in batch-wise mode or may be conducted in continuous mode, and for example, the zeolite catalyst may be immersed in the above-described solution containing an acid and stirred in a stirring tank, or the above-described solution containing an acid may be passed through a tubular vessel filled with the zeolite catalyst. In the case of the batch-wise mode, the acid treatment step can be conducted again after separation, however, the number of the acid treatment step is preferably once or more and 10 times or less.

After the above-described mixing step, or after performing the above-described mixing step and at least one step selected from the group consisting of the above-described washing step I and the above-described acid treatment step, a step of separating the product and the liquid by concentration, filtration, decantation and the like (separation step) or a step washing the zeolite catalyst (washing step II) may be conducted. By performing the above-described separation step and the above-described washing step II, a more purified zeolite catalyst can be obtained. The solvent used in the above-described washing step II includes organic solvents such as methanol, ethanol and the like, and water and the like. The temperature in the above-described washing step II is preferably 0° C. or more and 100° C. or less, and the pressure is preferably 0.1 MPa or more and 5 MPa or less. The time of the above-described washing step II is preferably 0.1 hour or more and 100 hours or less. The washing treatment may be conducted in batch-wise mode or may be conducted in continuous mode, and for example, the zeolite catalyst may be immersed in water or the like and stirred in a stirring tank, or water or the like may be passed through a tubular vessel filled with the zeolite catalyst. In the case of the batch-wise mode, the above-described washing step II can be conducted several times, however, the number of the above-described washing step II is preferably once or more and 10 times or less. In the above-described separation step, it is not necessary that the zeolite catalyst and the liquid are separated completely, and for example, it may be permissible that the zeolite catalyst and the liquid are separated to a certain extent by concentration, filtration, decantation and the like, then, dried appropriately, to obtain a zeolite catalyst.

The zeolite catalyst may be solid or slurry. Further, the zeolite catalyst may be supported on a carrier and used. The carrier includes metal oxides such as silica, alumina, titania, zirconia, ceria and the like, a mixture of two or more metal oxides, a composite oxide of two or more metals, and the like.

The zeolite catalyst may be molded to fit a reaction vessel and the like to be used. The molding method of the zeolite catalyst includes, for example, a method of molding by compressing a solid zeolite catalyst, a method of spraying a slurry-like zeolite catalyst and drying it, and the like. Further, after molding, the zeolite catalyst may be subjected to, for example, a contact treatment with water vapor, to improve the strength.

The ε-caprolactam production method of the present invention is a method comprising a step of Beckmann-rearranging cyclohexanone oxime in a gas phase in the presence of the above-described zeolite catalyst, and it is preferable to conduct a step of producing the above-described zeolite catalyst by a method including the above-described mixing step, before the step of Beckmann rearrangement. The method containing the above-described mixing step is preferably a method of conducting at least one step selected from the group consisting of the above-described washing step I, the above-described acid treatment step, the above-described separation step and the above-described washing step II, after the above-described mixing step.

The reaction temperature in the Beckmann rearrangement reaction is preferably 250° C. or more and 500° C. or less, more preferably 300° C. or more and 450° C. or less, and the reaction pressure is preferably 0.005 MPa or more and 0.5 MPa or less, more preferably 0.005 MPa or more and 0.2 MPa or less. The Beckmann rearrangement reaction may be conducted in fixed bed mode or may be conducted in fluidized bed mode. The supply rate of cyclohexanone oxime as a raw material is preferably 0.1 $h^{-1}$ or more and 20 $h^{-1}$ or less, more preferably 0.2 $h^{-1}$ or more and 10 $h^{-1}$ or less in terms of the supply rate (g/h) of cyclohexanone oxime per 1 g of the catalyst, that is, space velocity WHSV ($h^{-1}$).

Cyclohexanone oxime may be, for example, singly introduced into the reaction system, or introduced together with an inert gas such as nitrogen, argon, carbon dioxide and the like. Further, an ether is allowed to coexist as described in JP-A No. hei-2-250866, a lower alcohol is allowed to coexist as described in JP-A No. hei-2-275850, an alcohol and/or ether and water are allowed to coexist as described in JP-A No. hei-5-201965, ammonia is allowed to coexist as described in JP-A No. hei-5-201966, methylamine is allowed to coexist as described in JP-A No. hei-6-107627, and the like, are also effective.

Cyclohexanone oxime may be, for example, one prepared by oximation of cyclohexanone with hydroxylamine or its salt, one prepared by ammoximation of cyclohexanone with anmonia and hydrogen peroxide in the presence of titanosilicate and the like, or one prepared by oxidation of cyclohexylamine.

The Beckmann rearrangement reaction may be combined with a treatment of calcining the zeolite catalyst under an atmosphere of an oxygen-containing gas such as air and the like (catalyst calcination treatment). By this catalyst calcination treatment, carbonaceous substances deposited on the catalyst can be calcined and removed, and the conversion rate of cyclohexanone oxime and persistence of the selectivity of ε-caprolactam can be enhanced. For example, when the Beckmann rearrangement reaction is conducted in fixed bed mode, a method in which cyclohexanone oxime is, if necessary together with other components, supplied to a fixed bed mode reaction vessel filled with a solid catalyst and the Beckmann rearrangement reaction is performed, then, supply of cyclohexanone oxime is stopped, then, an oxygen-containing gas is supplied and calcination is performed, and further, the Beckmann rearrangement reaction and calcination are repeated is suitably adopted. Further, when the Beckmann rearrangement reaction is conducted in fluidized bed mode, a method in which cyclohexanone oxime is, if necessary together with other components, supplied to a fluidized bed mode reaction vessel in which a solid catalyst flows and while conducting the Beckmann rearrangement reaction, the solid catalyst is extracted from the reaction vessel continuously or intermittently, and calcined in a calcination vessel, then, returned to the reaction vessel again is suitably adopted.

The ε-caprolactam production method of the present invention may contain a step of conducting a post treatment of the resulting product, after the above-described step of the Beckmann rearrangement reaction. As the post treatment method, known methods can be appropriately adopted, and for example, the reaction product gas is cooled and condensed, then, ε-caprolactam is separated by extraction, distillation, crystallization and the like.

Examples of the present invention will be shown below, but the present invention is not limited to them. The space velocity WHSV ($h^{-1}$) of cyclohexanone oxime was calculated by dividing the supply rate (g/h) of cyclohexanone oxime by the weight (g) of the catalyst. Analysis of cyclohexanone oxime and ε-caprolactam was conducted by gas chromatography, and the conversion rate of cyclohexanone oxime and the selectivity of ε-caprolactam were calculated by the following formulae, respectively, in which the substance amount (mol) of cyclohexanone oxime supplied was expressed as X, the substance amount (mol) of unreactive cyclohexanone oxime was expressed as Y and the substance amount (mol) of ε-caprolactam generated was expressed as Z.

conversion rate (%) of cyclohexanone oxime= [(X−Y)/X]×100 selectivity (%) of ε-caprolactam=[Z/(X−Y)]×100

EXAMPLE 1

(a) Production Method of Zeolite Catalyst (A)

Twenty grams (20 g) of the zeolite produced by a method described in JP-A No. 2013-147356 was charged in an autoclave, and into this was added 556 g of a mixed liquid composed of 220 g of a 7.5% by mass ammonium nitrate aqueous solution, 336 g of a 25% by mass ammonia aqueous solution, 0.0106 g of magnesium nitrate hexahydrate and 0.0056 g of tetrapropylammonium bromide, and stirred at 90° C. for 1 hour, then, a solid was separated by filtration. For this solid, the same treatment with a mixed liquid of an ammonium nitrate aqueous solution, an ammonia aqueous solution, magnesium nitrate hexahydrate and tetrapropylammonium bromide as described above was repeated twice, then, washed with water and dried, to obtain a zeolite catalyst (A). As a result of analysis by the ICP-MS method, the concentration of Mg in the zeolite catalyst (A) was 170 ppm by mass.

(b) Production of ε-Caprolactam

The above-described zeolite catalyst (A) (0.375 g) was filled in a quartz glass reaction tube having an internal diameter of 1 cm to form a catalyst layer, and preheated at 350° C. for 1 hour under a nitrogen flow of 4.2 L/h. Then, under a nitrogen flow of 4.2 L/h, the temperature of the catalyst layer was decreased to 327° C., then, a vaporized mixture of cyclohexanone oxime/methanol=1/1.8 (weight ratio) was supplied to a reaction tube at a supply rate of 8.4 g/h (cyclohexanone oxime WHSV=8 h$^{-1}$), and reacted. After 6 hours and 15 minutes from start of supply of the mixture, the reaction gas in 15 minutes (from 6 hours and 15 minutes to 6 hours and 30 minutes after start of supply (the total reaction time: 6.5 hours)) was collected, and analyzed by gas chromatography, the conversion rate of cyclohexanone oxime and the selectivity of ε-caprolactam were calculated. As a result, the conversion rate of cyclohexanone oxime was 100.0% and the selectivity ε-caprolactam was 95.6%. Further, the reaction rate constant was calculated from the conversion rate of cyclohexanone oxime. Next, the temperature of the catalyst layer was raised up to 430° C. and the catalyst was calcined in air at the same temperature for 13 hours, then, the temperature of the catalyst layer was decreased to 327° C., and a vaporized mixture of cyclohexanone oxime/methanol=1/1.8 (weight ratio) was supplied to a reaction tube at the same supply rate as described above, and reacted again. After 6 hours and 15 minutes from start of supply of the mixture again, the reaction gas in 15 minutes (from 6 hours and 15 minutes to 6 hours and 30 minutes after start of supply (the total reaction time: 13 hours)) was collected, and the conversion rate of cyclohexanone oxime and the selectivity of ε-caprolactam were calculated by the same manner, and the reaction rate constant was calculated from the conversion rate of cyclohexanone oxime. Further, the temperature of the catalyst layer was raised up to 430° C., and the catalyst was calcined in air at the same temperature for 13 hours, then, the temperature of the catalyst layer was decreased to 327° C., and a vaporized mixture of cyclohexanone oxime/methanol=1/1.8 (weight ratio) was supplied to a reaction tube at the same supply rate as described above, and reacted again. After 6 hours and 15 minutes after start of supply of the mixture again, the reaction gas in 15 minutes (from 6 hours and 15 minutes to 6 hours and 30 minutes after start of supply (the total reaction time: 19.5 hours)) was collected, and the conversion rate of cyclohexanone oxime and the selectivity of ε-caprolactam were calculated in the same manner, and the reaction rate constant was calculated from the conversion rate of cyclohexanone oxime. One cycle from the step of raising the temperature of the catalyst layer up to 430° C. to the step of calculating the conversion rate of cyclohexanone oxime and the selectivity of ε-caprolactam was repeated. The results of plotting of the reaction rate constant at each total reaction time are shown in FIG. 1. The total reaction time is the sum from after start of supply of the mixture to completion of collection of the reaction gas in each cycle, excluding the time for raising the temperature of the catalyst layer up to 430° C., the time for decreasing the temperature of the catalyst layer to 327° C. after calcination in air at the same temperature for 13 hours and the time for calculating the conversion rate of cyclohexanone oxime and the selectivity of ε-caprolactam.

EXAMPLE 2

(a) Production Method of Zeolite Catalyst (A-2)

Twenty four grams (24 g) of the zeolite produced by a method described in JP-A No. 2013-147356 was charged in an autoclave, and into this was added 667 g of a mixed liquid composed of 264 g of a 7.5% by mass ammonium nitrate aqueous solution, 403 g of a 25% by mass ammonia aqueous solution, 0.0025 g of magnesium nitrate hexahydrate and 0.0067 g of tetrapropylammonium bromide, and stirred at 90° C. for 1 hour, then, a solid was separated by filtration. For this solid, the same treatment with a mixed liquid of an ammonium nitrate aqueous solution, an ammonia aqueous solution, magnesium nitrate hexahydrate and tetrapropylammonium bromide as described above was repeated twice, then, washed with water and dried, to obtain a zeolite catalyst (A-2). As a result of analysis by the ICP-AES method, the concentration of Mg in the zeolite catalyst (A-2) was 36 ppm by mass.

(b) Production of ε-Caprolactam

The above-described zeolite catalyst (A-2) (0.375 g) was filled in a quartz glass reaction tube having an internal diameter of 1 cm to form a catalyst layer, and preheated at 350° C. for 1 hour under a nitrogen flow of 4.2 L/h. Then, under a nitrogen flow of 4.2 L/h, the temperature of the catalyst layer was decreased to 327° C., then, a vaporized mixture of cyclohexanone oxime/methanol=1/1.8 (weight ratio) was supplied to a reaction tube at a supply rate of 8.4 g/h (cyclohexanone oxime WHSV=8 h$^{-1}$), and reacted. After 6 hours and 15 minutes from start of supply of the mixture, the reaction gas in 15 minutes (from 6 hours and 15 minutes to 6 hours and 30 minutes after start of supply (the total reaction time: 6.5 hours)) was collected, and analyzed by gas chromatography, the conversion rate of cyclohexanone oxime and the selectivity of ε-caprolactam were calculated. As a result, the conversion rate of cyclohexanone oxime was 100.0% and the selectivity ε-caprolactam was 96.1%. Next, the temperature of the catalyst layer was raised up to 430° C. and the catalyst was calcined in air at the same temperature for 13 hours, then, the temperature of the catalyst layer was decreased to 327° C., and a vaporized mixture of cyclohexanone oxime/methanol=1/1.8 (weight ratio) was supplied to a reaction tube at the same supply rate as described above, and reacted again. After 6 hours and 15 minutes from start of supply of the mixture again, the reaction gas in 15 minutes (from 6 hours and 15 minutes to 6 hours and 30 minutes after start of supply (the total reaction time: 13 hours)) was collected, and the conversion rate of cyclohexanone oxime was calculated by the same manner. Further, the temperature of the catalyst layer was raised up to 430° C., and the catalyst was calcined in air at the same temperature for 13 hours, then, the temperature of the catalyst layer was decreased to 327° C., and a vaporized mixture of cyclohexanone oxime/methanol=1/1.8 (weight ratio) was supplied to a reaction tube at the same supply rate as described above, and reacted again. After 6 hours and 15 minutes after start of supply of the mixture again, the reaction gas in 15 minutes (from 6 hours and 15 minutes to 6 hours and 30 minutes after start of supply (the total reaction time: 19.5 hours)) was collected, and the conversion rate of cyclohexanone oxime was calculated in the same manner. One cycle from the step of raising the temperature of the catalyst layer up to 430° C. to the step of calculating the conversion rate of cyclohexanone oxime and the selectivity of ε-caprolactam was repeated. The results of plotting of the conversion rate of cyclohexanone oxime at each total reaction time are shown in FIG. 3. The total reaction time is the sum from after start of supply of the mixture to completion of collection of the reaction gas in each cycle, excluding the time for raising the temperature of the catalyst layer up to 430° C., the time for decreasing the temperature of the catalyst layer to 327° C. after calcination in air at the same temperature for 13 hours and the time for calculating the conversion rate of cyclohexanone oxime and the selectivity of ε-caprolactam.

EXAMPLE 3

(a) Production Method of Zeolite Catalyst (A-3)

Eight grams (8 g) of the zeolite produced by a method described in JP-A No. 2013-147356 was charged in an autoclave, and into this was added 223 g of a mixed liquid composed of 88 g of a 7.5% by mass ammonium nitrate aqueous solution, 134.4 g of a 25% by mass ammonia aqueous solution and 0.1266 g of magnesium nitrate hexahydrate, and stirred at 90° C. for 1 hour, then, a solid was separated by filtration. For this solid, the same treatment with a mixed liquid of an ammonium nitrate aqueous solution, an ammonia aqueous solution and magnesium nitrate hexahydrate as described above was repeated twice, then, washed with water and dried, to obtain a zeolite catalyst (A-3). As a result of analysis by the ICP-AES method, the concentration of Mg in the zeolite catalyst (A-3) was 4000 ppm by mass.

(b) Production of ε-Caprolactam

The same reaction as in Example 2 was carried out except that the above-described zeolite catalyst (A-3) was used. When the total reaction time was 6.5 hours, the conversion rate of cyclohexanone oxime was 100.0%, and the selectivity of ε-caprolactam was 95.0%. The results of plotting of the conversion rate of cyclohexanone oxime at each total reaction time are shown in FIG. 3.

EXAMPLE 4

(a) Production Method of Zeolite Catalyst (A-4)

Twenty four grams (24 g) of the zeolite produced by a method described in JP-A No. 2013-147356 was charged in an autoclave, and into this was added 667 g of a mixed liquid composed of 264 g of a 7.5% by mass ammonium nitrate aqueous solution, 403.2 g of a 25% by mass ammonia aqueous solution and 0.0067 g of tetrapropylammonium bromide, and stirred at 90° C. for 1 hour, then, a solid was separated by filtration. For this solid, the same treatment with a mixed liquid of an ammonium nitrate aqueous solution, an ammonia aqueous solution and tetrapropylammonium bromide as described above was further repeated once, to obtain a solid. This solid was charged in an autoclave, and into this was added 223 g of a mixed liquid composed of 264 g of a 7.5% by mass ammonium nitrate aqueous solution, 403.2 g of a 25% by mass ammonia aqueous solution, 0.0067 g of tetrapropylammonium bromide and 0.0013 g of magnesium nitrate hexahydrate, and stirred at 90° C. for 1 hour, then, a solid was separated by filtration. This solid was washed with water and dried, to obtain a zeolite catalyst (A-4). As a result of analysis by the ICP-MS method, the concentration of Mg in the zeolite catalyst (A-4) was 8.0 ppm by mass.

(b) Production of ε-Caprolactam

The same reaction as in Example 2 was carried out except that the above-described zeolite catalyst (A-4) was used. When the total reaction time was 6.5 hours, the conversion rate of cyclohexanone oxime was 100.0%, and the selectivity of ε-caprolactam was 96.0%. The results of plotting of the conversion rate of cyclohexanone oxime at each total reaction time are shown in FIG. 3.

EXAMPLE 5

(a) Production Method of Zeolite Catalyst (A-5)

[Step (A)]

Into a glass beaker were charged 115 g of tetraethyl orthosilicate [Si(OC$_2$H$_5$)$_4$], 105 g of a 39.7% by weight tetra-n-propylammonium hydroxide aqueous solution (containing 0.9% by weight potassium, 1.0% hydrogen bromide, 58.4% by weight water), 3.4 g of boric acid, 0.13 g of potassium hydroxide and 118 g of water, and stirred vigorously at room temperature for 120 minutes, to obtain a mixture. The amount of a silicon element contained in the resultant mixture was 10.0 mol with respect to 1 mol of a boron element contained in the above-described mixture.

[Step (B)]

The mixture obtained the above-described step (A) was charged in a stainless autoclave and stirred at 140° C. for 24 hours, to perform a hydrothermal synthesis reaction. The resultant reaction mixture was filtrated, and washed with ion exchanged water several times until pH of the washing liquid became 9, then, dried at 100° C. or more. The resultant crystal was calcined at 530° C. for 1 hour under nitrogen flow, then, calcined at 530° C. for 1 hour under flow, to obtain a zeolite crystal.

[Step (C)]

The resultant zeolite crystal (10.0 g) was charged in an autoclave, and into this was added 300 g of a 0.2 mol/L nitric acid aqueous solution, and the mixture was stirred at 90° C. for 1 hour, then, the crystal was separated by filtration. For this zeolite crystal, the same treatment with a nitric acid aqueous solution as described above was further repeated twice, then, washed with ion exchanged water several times until pH of the washing liquid became 5 and dried at 100° C. or more, to obtain zeolite.

[Step (D)]

Five grams (5 g) of the zeolite obtained in the above-described step (C) was charged in an autoclave, and into this was added 139 g of a mixed liquid composed of 8.3 g of a 25% by mass ammonia aqueous solution, 0.0156 g of magnesium nitrate hexahydrate and 130.7 g of water, and stirred at 90° C. for 1 hour, then, the solid was separated by filtration. This solid was washed with water and dried, to obtain a zeolite catalyst (A-5). As a result of analysis by the ICP-AES method, the concentration of Mg in the zeolite catalyst (A-5) was 180 ppm by mass.

(b) Production of ε-Caprolactam

The same reaction as in Example 2 was carried out except that the above-described zeolite catalyst (A-5) was used. When the total reaction time was 6.5 hours, the conversion rate of cyclohexanone oxime was 99.7%, and the selectivity of ε-caprolactam was 96.1%. The results of plotting of the conversion rate of cyclohexanone oxime at each total reaction time are shown in FIG. 3.

COMPARATIVE EXAMPLE 1

(a) Production of Zeolite Catalyst (B)

Ten grams (10 g) of the zeolite produced by a method described in JP-A No. 2013-147356 was charged in an autoclave, and into this was added 278 g of a mixed liquid composed of 110 g of a 7.5% by mass ammonium nitrate aqueous solution, 168 g of a 25% by mass ammonia aqueous solution and 0.0028 g of tetrapropylammonium bromide, and stirred at 90° C. for 1 hour, then, a solid was separated by filtration. A zeolite catalyst (B) was obtained in the same manner as in Example 1 except that this solid was used.

(b) Production of ε-Caprolactam

The same reaction as in Example 1 was carried out using the zeolite catalyst (B) obtained in (a) described above. When the total reaction time was 6.5 hours, the conversion rate of cyclohexanone oxime was 100.0%, and the selectivity of ε-caprolactam was 96.2%. The results of plotting of the reaction rate constant at each total reaction time are shown in FIG. 1.

COMPARATIVE EXAMPLE 2

(a) Production Method of Zeolite Catalyst (B-2)

Eight grams (8 g) of the zeolite produced by a method described in JP-A No. 2013-147356 was charged in an autoclave, and into this was added 223 g of a mixed liquid composed of 88 g of a 7.5% by mass ammonium nitrate aqueous solution, 134.4 g of a 25% by mass ammonia aqueous solution and 0.3799 g of magnesium nitrate hexahydrate, and stirred at 90° C. for 1 hour, then, a solid was separated by filtration. For this solid, the same treatment with a mixed liquid of an ammonium nitrate aqueous solution, an ammonia aqueous solution and magnesium nitrate hexahydrate as described above was further repeated twice, then, washed with water and dried, to obtain a zeolite catalyst (B-2). As a result of analysis by the ICP-AES method, the concentration of Mg in the zeolite catalyst (B-2) was 17000 ppm by mass.

(b) Production of ε-Caprolactam

The same reaction as in Example 2 was carried out except that the above-described zeolite catalyst (B-2) was used. When the total reaction time was 6.5 hours, the conversion rate of cyclohexanone oxime was 99.9%, and the selectivity of ε-caprolactam was 93.8%. The results of plotting of the conversion rate of cyclohexanone oxime at each total reaction time are shown in FIG. 3.

Changes of the reaction rate constant in Example 1 and Comparative Example 1 are shown in FIG. 1. The reaction rate constant ($s^{-1}$) was determined by the following formula in which the conversion rate of cyclohexanone oxime is expressed as $\chi$ (%) and the space velocity of cyclohexanone oxime is expressed as WHSV ($h^{-1}$).

reaction rate constant ($s^{-1}$)=−ln(1−$\chi$/100)×(WHSV/3600)

In the formula, ln(1−$\chi$/100) represents the natural logarithm of (1−$\chi$/100). The space velocity WHSV ($h^{-1}$) of cyclohexanone oxime was calculated by dividing the supply rate (g/h) of cyclohexanone oxime by the weight (g) of the catalyst.

As shown in FIG. 1, when ε-caprolactam is produced using the zeolite catalyst of Example 1, the initial reaction rate constant is high and high reaction rate constant is maintained for a long period of time as compared with use of the zeolite catalyst of Comparative Example 1. From these results, it is understood that the ε-caprolactam production method of the present invention is excellent in productivity since the initial catalytic activity is high and high catalytic activity can be maintained for a long period of time.

Changes of the conversion rate of cyclohexanone oxime in Example 2 to 5 and Comparative Example 2 are shown in FIG. 3. As shown in FIG. 3, while the conversion rate decreases to less than 99.0% at a total reaction time of 160 hours in Comparative Example 2, the conversion rate not lower than 99.0% is maintained even if the total reaction time is over 160 hours in Example 2 to 5. As described above, when ε-caprolactam is produced using the zeolite catalysts of Example 2 to 5, high conversion rate is maintained over a long period of time as compared with use of the zeolite catalyst of Comparative Example 2. From these results, it is understood that the ε-caprolactam production method of the present invention is excellent in productivity since high catalytic activity can be maintained for a long period of time. Further, particularly when ε-caprolactam is produced using the zeolite catalysts of Example 1, Example 2, Example 4 and Example 5, the initial selectivity is also high in addition to the above-described excellent productivity.

The invention claimed is:

1. A production method of ε-caprolactam, comprising a step of Beckmann-rearranging cyclohexanone oxime in a gas phase in the presence of a zeolite catalyst containing a silicon element and at least one element selected from the group consisting of alkaline earth metal elements and a magnesium element, wherein the concentration of the at least one element selected from the group consisting of alkaline earth metal elements and a magnesium element in the zeolite catalyst is 3 ppm by mass or more and 10000 ppm by mass or less.

2. The production method of ε-caprolactam according to claim 1, further comprising a step of producing the zeolite catalyst by a method containing the following mixing step:

Mixing step: a step of mixing zeolite with a solution containing a compound having at least one element selected from the group consisting of alkaline earth metal elements and a magnesium element.

3. The production method of ε-caprolactam according to claim 2, wherein said zeolite has a pentasil type structure.

4. The production method of ε-caprolactam according to claim 2, wherein said zeolite is zeolite having nest silanol, and said zeolite having nest silanol is produced by a method containing the following step (1) and the following step in this order:

Step (1): a step of reacting a mixture containing a silicon compound and at least one compound selected from the group consisting of boron compounds and germanium compounds, to obtain a zeolite crystal;

Step (2): a step of contact-treating the zeolite crystal with an aqueous solution containing at least one acid selected from the group consisting of inorganic acids and organic acids.

5. The production method of ε-caprolactam according to claim 1, wherein said zeolite catalyst contains a magnesium element.

* * * * *